US006811706B1

(12) United States Patent
Wahlberg

(10) Patent No.: US 6,811,706 B1
(45) Date of Patent: Nov. 2, 2004

(54) ACTIVATED SLUDGE PROCESS OPTIMIZATION

(76) Inventor: Eric J. Wahlberg, Brown and Caldwell 3480 Bushkirk Ave., Suite 150, Pleasant Hill, CA (US) 94523-4342

(*) Notice: Subject to any disclaimer, the term of this patent is extended or adjusted under 35 U.S.C. 154(b) by 0 days.

(21) Appl. No.: 09/564,343

(22) Filed: May 3, 2000

Related U.S. Application Data

(60) Provisional application No. 60/132,870, filed on May 5, 1999.

(51) Int. Cl.[7] .................................................. C02F 3/00
(52) U.S. Cl. ..................... 210/739; 210/740; 210/143; 73/61.68
(58) Field of Search ................. 73/61.68; 210/739–740, 210/143; 702/188

(56) References Cited

U.S. PATENT DOCUMENTS

| | | |
|---|---|---|
| 2,154,132 A | 4/1939 | Mallory |
| 3,746,167 A | 7/1973 | Arthur |
| 3,869,903 A * | 3/1975 | Beach et al. ............... 73/61.65 |
| 4,130,481 A | 12/1978 | Chase et al. |
| 4,168,233 A | 9/1979 | Anderson |
| 4,170,553 A | 10/1979 | Lang et al. |
| 4,859,341 A | 8/1989 | Schreiber |
| 5,076,928 A | 12/1991 | Ballnus |
| 5,173,187 A | 12/1992 | Nader et al. |
| 5,233,876 A | 8/1993 | LaPack et al. |
| 5,242,592 A | 9/1993 | Ballnus |
| 5,324,431 A | 6/1994 | Watanabe et al. |
| 5,421,995 A | 6/1995 | Norcross |
| 5,589,068 A | 12/1996 | Nielsen |
| 5,601,704 A | 2/1997 | Salem et al. |
| 5,733,456 A | 3/1998 | Okey et al. |

FOREIGN PATENT DOCUMENTS

JP   01315393 A  * 12/1989  ............. C02F/3/12

OTHER PUBLICATIONS

*Chemical Engineers Handbook*, 5th Edn., 1973, p. 19–6.*
Wahlberg, E.J., Activated Sludge Bioflocculation: Measurement, Influencing Facors, and Physical Enhancement, Ph.D. dissertation, Clemson University, May 1992, pp. ii–iv and 31–33, 46–51, 85–87, 104–112, 122–124.
Wahlberg, E.J. and Parker, D.S. Troubleshooting Activated Sludge Secondary Clarifier Performance with Simple Diagnostic Tests, Florida Water Resources Conference, Tampa, Florida, Aug. 28–31, 1994, pp. 1–7.
Wahlberg, E.J., Keinath, T.M. and Parker, D.S. Influence of activated sludge flocculation time on secondary clarification, Water Environment Research, 66(6), Sep./Oct. 1994, pp. 779–786.
Wahlberg, E.J., Bower J., Bittner, M. and Margolis, Z. Al West Meets W. Deming: A Statistical Approach to the Control of the Activated Sludge Process, WEFTEC'94, Water Environment Federation 67th Annual Conference & Exposition, Chicago, Illinois, Oct. 15–19, 1994, pp. 259–270.
Water Environment Federation, Operation of Municipal Wastewater Treatment Plants, Manual of Practice No. 11, Fifth Edition, 1996, Water Environment Federation: Alexandria, Virginia, pp. 571–613, 646–675 and 688–689.
Wahlberg, E.J., Crowley, J.P., Bower, J., Bittner, M. and Margolis, Z. in Why the Activated Sludge Process Is So Hard to Operate: Modeling Brings New Light to Operations, WEFTEC'96, Water Environment Federation 69th Annual Conference & Exposition, Dallas, Texas, Oct. 5–9, 1996.

* cited by examiner

Primary Examiner—Chester T. Barry
(74) Attorney, Agent, or Firm—Robert M. Hunter

(57) ABSTRACT

An apparatus and a method for controlling and optimizing the performance of the activated sludge process and the plant or process so controlled by measuring the parameters of most importance over time, i.e., the sludge's settling, compacting, and flocculating characteristics; manipulating said measurements to determine whether changes in them are significant; processing the changes; and taking appropriate control actions.

42 Claims, 4 Drawing Sheets

ACTIVATED SLUDGE PROCESS OPTIMIZATION

CROSS-REFERENCE TO RELATED APPLICATIONS

This application claims the benefit of U.S. Provisional Application No. 60/132,870, filed May 5, 1999, the disclosure of which application is incorporated by reference as if fully set forth herein.

STATEMENT REGARDING FEDERALLY SPONSORED RESEARCH OR DEVELOPMENT

Not Applicable

BACKGROUND OF THE INVENTION

This invention relates to an apparatus and method for optimizing the performance of biological processes for wastewater treatment. In particular, the invention relates to optimization of the activated sludge process.

A variety of process combinations are used to treat wastewater before it is reused or discharged to the environment. Many of these combinations incorporate the activated sludge process. The activated sludge process was invented in the early 1900s by Ardern and Lockett (Ardem, E. and Lockett, W. T., "Experiments on the oxidation of sewage without the aid of filters," *Journal of the Society of Chemical Industries*, 33, 523, 1914). Today, it is the most commonly used process for treating industrial and municipal wastewaters. The activated sludge process has many variations, including conventional activated sludge, extended aeration, pure oxygen activated sludge, step-feed, sludge reaeration, contact stabilization, and the solids contact step in the trickling filter/solids contact process, etc.

In the activated sludge process, wastewater is introduced to a biological reactor, termed an "aeration tank" or "aeration basin," that contains a suspended culture of microorganisms, often termed "biomass." The culture of microorganisms is often termed "activated sludge" and the mixture of the microorganism culture and the wastewater is often called "mixed liquor." After the wastewater is in contact with the activated sludge for a period of time sufficient for treatment to have occurred, the mixed liquor is discharged to a secondary clarifier in which flocculation and settling of the sludge occurs to form a sludge blanket. During activated sludge treatment, the biomass in the system increases as particulate and soluble organic materials in the wastewater are converted into biomass by the microorganisms. Most of the settled activated sludge, often termed "return activated sludge" or "RAS," is returned to the aeration tank. A small portion, often termed "waste activated sludge" or "WAS," is removed from the process.

The performance of the activated sludge process can be significantly affected by the design of its unit operations (e.g., aeration and clarification) and by the manipulation of one or men more of three primary control variables: aeration rate, return activated sludge flow rate and waste activated sludge flow rate. Operation of the activated sludge process is optimized when those independent variables are correctly manipulated within a range of values. Since its inception to approximately the 1960s, the design of the activated sludge process was based primarily on experience, rules of thumb, process loading factors, etc. In the 1970s, the understanding of bacterial growth kinetics greatly advanced a more scientific approach to the design of activated sludge systems. With this knowledge it became apparent—and is now universally recognized—that the growth rate of the microbial culture in the activated sludge process is the design and operational variable of most importance.

In essence, the microbial growth rate of activated sludge is the inverse of the mean cell residence time (known also as the sludge age, solids residence time, MCRT, or SRT). The MCRT is calculated by dividing the mass of microorganisms residing in an activated sludge system [typically taken as the mixed liquor total suspended solids (MLSS) or the mixed liquor volatile suspended solids (MLVSS)] by the mass of microorganisms removed—intentionally in the WAS stream and unintentionally in the secondary effluent steam—from the system per day.

Controlling the activated sludge process, like its design, has evolved since its inception. In the 1960s and 1970s, Alfred W. (Al) West of the U.S. Environmental Protection Agency (USEPA) developed control techniques that were initially based on sludge quality (West, A. W., *Operational Control Procedures for the Activated Sludge Process, Part 1, Observations*, Environmental Protection Agency Report No. EPA-330/9-74-001-a, April 1973). Three important elements of Al West's techniques were a settlometer test, a centrifuge spin test, and a measurement of the secondary effluent turbidity. The settlometer test is conducted by collecting a sample of mixed liquor (i.e., the aeration basin contents) as it exits the aeration basin, shaking it, pouring it into a settling container, and recording the solids/liquid interface height (or depth) with respect to time, typically 0, 5, 10, 15, 20, 25, 30, 40, 50, and 60 minutes. The two most commonly used settling containers used are a I-liter (L) graduated cylinder and a 2-L Mallory settlometer. Although any container can be used (any see-through container, e.g., a canning jar), the 2-L Mallory settlometer is the most widely used today and is the container recommended by Al West. An important step in this procedure is plotting the interface height as a function of settling time and noting the general shape of the settling curve to ascertain the sludge's settling characteristics.

The second key procedure to Al West's techniques is the centrifuge spin test. In this test, an aliquot of the mixed liquor sample used in the settlometer test is centrifuged for 15 minutes and the percent volume of the initial aliquot volume occupied by the solids is recorded. He referred to this percentage as the "aeration tank concentration" or "ATC." The ATC was used as a surrogate for the mixed liquor suspended solids concentration, despite the fact that the ATC is a function of both the solids concentration and the structural integrity of the microbial cells and extracellular materials (e.g., the compressibility of the solids).

Finally, a sample of the secondary clarifier effluent is collected. The turbidity of this sample is measured because turbidity is much more quickly measured than the total suspended solids concentration.

There are at least two limitations of using Al West's procedures to guide operation of the activated sludge process. First, while the compaction characteristics of a sludge are important, nowhere in an activated sludge system are the solids subjected to the multiple gravitational forces occurring in the centrifuge test Activated sludge solids are separated in almost all cases by gravity, so how the sludge compacts by simple settling is more appropriate. Second, the turbidity of the secondary clarifier effluent is confounded by the performance of the secondary clarifier(s). For this reason, it is inappropriate to use secondary clarifier effluent turbidity to quantify the flocculation characteristics of the activated sludge solids. Secondary effluent turbidity is, however, useful for quantifying the performance of the secondary clarifier when compared to the supernatant turbidity after the entering mixed liquor is flocculated and settled.

As the microbial growth kinetic approach to the design of activated sludge processes gained momentum, Al West expanded his approach to process control to take into account biomass growth kinetics. His approach is essentially one of controlling the SRT of the process.

Today, most approaches to activated sludge process control are based on growth kinetics. Essentially, the growth rate is controlled by one of three methods: (1) maintaining a constant SRT (or MCRT or sludge age), (2) maintaining a constant food-to-microorganism (F:M) ratio, or (3) maintaining a constant mixed liquor suspended solids or mixed liquor volatile suspended solids concentration or mass. For a variety of reasons (e.g., operator lack of understanding, influent variability, etc.), this approach is not working well.

The USEPA and others have documented the poor overall performance of the Nation's activated sludge treatment plants. One EPA study (*Environmental Protection Agency Report No. EPA*-600/2-79-034) found that 50 to 90 percent of the plants investigated regularly violate treatment standards. That document also references earlier EPA studies that reported that a third to a half of wastewater treatment plants do not meet the standards for which they were built. Even though these studies were published 20 years ago, their findings are still relevant today for a very simple reason: activated sludge plants are becoming increasingly more difficult to operate due to the imposition of more stringent permit requirements, for example, nutrient removal. Clearly, the USEPA has documented the existence of a large unsolved problem. The problem is aggravated by the fact that quantification of unit process performance variability in activated sludge systems has been incompletely documented. Variability in effluent quality, on the other hand, has been studied. For example, many investigators have reported that effluent total suspended solids (TSS) and biochemical oxygen demand (BOD) concentrations follow a log normal distribution.

This disclosure shows that the problems associated with poor activated sludge process performance are primarily a function of two things: lack of activated sludge process understanding and over control of the activated sludge process. In attempting to control the growth rate of the activated sludge biomass by any of the common methods, an operator is, in essence, attempting to grow an activated sludge that settles, compacts, and flocculates well. The problem is that a test to measure a sludge's settling, compacting, and flocculating characteristics is still not available. Operators' focus on the growth rate is, therefore, one of convenience: because the SRT (or F:M or mixed liquor suspended solids concentration or mass) is measurable and the settling, compacting, and flocculating characteristics are not, operators focus on the former and "hope" they get the latter. The fact remains, however, that sludge quality (i.e., its settling, compacting, and flocculating characteristics) is the parameter of utmost importance to activated sludge treatment plant performance.

The disclosures of a number of U.S. patents explain the activated sludge process and teach a variety of approaches to controlling the activated sludge process. The disclosures of the following U.S. patents is incorporated herein by reference as is fully set forth.

Mallory (U.S. Pat. No. 2,154,132) discloses a number of processes for controlling the activated sludge process. One process involves determining the suspended solids concentrations of both the return activated sludge and the aerated mixed liquor and manipulating the ratio of those concentrations to ensure that the ratio is substantially equal to the ratio between the aerator(s) volume and clarifier(s) volume, minus one (a value he calls "the plant constant"). Another process involves determining the depth of the sludge blanket in the clarifier(s) and the amount of suspended solids in the aerator(s) and clarifier(s) and manipulating the ratio of those amounts to ensure that the ratio is substantially equal to the plant constant. A further process involves determining the ratio between the clarifier(s) volume and the volume of the sludge blanket and manipulating that ratio to be equal to the plant constant. Yet another process involves determining the ratio between the rate of effluent flow and the rate of return sludge flow and manipulating that ratio to be equal to twice the aerator(s) volume divided by the clarifier(s) volume, minus two. Another process involves determining the concentration of suspended solids in the aerated mixed liquor as it settled to form a sludge blanket and ensuring that the rate of increase in the concentration of suspended solids in the settling mixed liquor conforms to a specified straight line rate. In this process, the rate of increase in the concentration of suspended solids in the settling mixed liquor may be determined by measuring the rate at which the volume of the sludge blanket (as revealed by the location of the liquid/solids interface) in an unflocculated sample of mixed liquor decreases in a graduated cylinder. The reference also teaches the use of a centrifuge to measure suspended solids concentrations as an alternative to the conventional technique of measuring the dry weight of the solids.

The activated sludge process control techniques of the Mallory reference are limited in that many of the techniques require that multiple mixed liquor, waste activated sludge and/or return activated sludge suspended solids samples be taken and multiple concentration measurements to be made on those samples, measurements which are time-consuming, difficult to replicate and require special equipment. Other Mallory techniques require that measurements be made of the depth of the sludge blanket in the clarifiers, also a difficult measurement. None of the techniques involve measurement of the clarity of the supernatant above the sludge blanket in a sample of mixed liquor that has been previously flocculated as an indication of the flocculating character of the mixed liquor. Thus, the reference teaches away from a process control technique based on characterization of activated sludge settling, compacting and flocculating character.

Arthur (U.S. Pat. No. 3,746,167) discloses a method and apparatus for determining the amount of settleable and suspended solids in a liquid, said method and apparatus involving a filtration step. This reference is limited in that filtration of a wastewater sample through filters that can only be used once is required, rendering the method labor intensive. Moreover, the reference does not teach how to use the measurements to control the activated sludge process.

Chase et al. (U.S. Pat. No. 4,130,481) discloses a computer-implemented system for controlling the return rate of activated sludge flow in order to maintain the density of activated sludge in the aeration tank at an optimum value. Measured quantities include carbon dioxide respiration rate, aeration air flow rate, and the densities of mixed liquor and returned and stored activated sludge. This reference is limited in that a variety of complex analyzers are required, including a non-dispersive infrared analyzer. Moreover, the only process control technique used is varying the return activated sludge return rate, which ignores the importance of varying the waste activated sludge rate and the aeration rate to optimize the operation of the activated sludge process.

The sludge volume index is mentioned, but only as a measure of the effectiveness of settling. No measurements of the character of activated sludge in the system are collected for use as inputs to control of the system.

Anderson (U.S. Pat. No. 4,168,233) discloses a system for automatically extracting samples of aeration tank mixed liquor and returned activated sludge, delivering a sample of mixed liquor to a settlometer jar for measurement of the sludge settling rate and delivering both a sample of mixed liquor and a sample of return activated sludge to a centrifuge for measurement of suspended solids concentrations. The solids/liquid interface in the settleometer is measured using a photo transistor sensing device (preferably, at 5 minute intervals for the first 30 minutes and at 10 minute intervals for the last 30 minutes), and the resulting settling curve is printed out. The reference suggests that the results of the testing can be used to develop control signals to vary the return activated sludge rate and/or the waste activated sludge rate (but not the aeration rate), but does not teach how to accomplish the critical step of using the collected data to affect activated sludge process control. The system of Anderson is limited in that no measurement is made of the height of the solids/liquid interface at set times in multiple, sequential samples and no measurement is made of the clarity (turbidity or suspended solids concentration) of settlometer supernatant (and, in fact, the supernatant is assumed to be "clear"). Thus, no measurement of the settling, compacting and flocculating character of the activated sludge is made. It is also limited in that a complicated apparatus (an automated centrifuge) must be used to measure sludge suspended solids concentrations.

Lang et al. (U.S. Pat. No. 4,170,553) disclose a process and apparatus for controlling the flocculation of foreign substances in a liquid that involves measurement of the turbidity of liquid drawn off from the process. The turbidity measurement is used to determine how much flocculating agent to add to the liquid for optimum treatment. This reference is limited in that it does not teach a system and method for control of the activated sludge process, but rather teaches control of a chemical flocculation step for water or wastewater.

Schreiber (U.S. Pat. No. 4,859,341) discloses a method for controlling an activated sludge process that involves measurement of the turbidity of clarified activated sludge obtained from the aeration tank and the concentration of dissolved oxygen in the aeration tank. The reference is limited in that it does not teach how a "clarified water" is to be obtained from an "activated water-sludge mixture." The reference is further limited in that the settling, compacting and flocculating characteristics of the activated sludge are not measured.

Ballnus (U.S. Pat. No. 5,076,928) discloses a method for controlling the aeration of an activated sludge in a tank that involves measurement of the turbidity, biochemical oxygen demand or chemical oxygen demand of clarified liquid obtained from the tank. Reference is made in this patent to a prior U.S. patent by the same inventor (U.S. Pat. No. 4,333,838) which teaches using a "centrifuge or decanter" to clarify liquid obtained from an aeration tank before the visible depth or turbidity of liquid is measured. These references are limited in that the settling, compacting and flocculating characteristics of the activated sludge are not measured.

Nader et al. (U.S. Pat. No. 5,173,187) discloses a method for controlling the biological clarifications stage of an activated sludge plant by monitoring the amount of certain microorganisms present using fluorescence-labeling and flow cytometry. This reference is limited by the use of complex measurement techniques to quantify the amount of particular "problem" microorganisms that are present in an activated sludge.

LaPack et al. (U.S. Pat. No. 5,233,876) disclose an apparatus and methods for on-line analysis of the influent and effluent of gas, liquid and both gas and liquid process streams. This reference is limited in that the settling, compacting and flocculating characteristics of the activated sludge are not measured.

Ballnus (U.S. Pat. No. 5,242,592) discloses a method for controlling the aerator of an activated sludge tank that involves measurement of the turbidity in the wastewater and phosphate concentration in the mixed liquor suspended solids. This reference is limited in that the settling, compacting and flocculating characteristics of the activated sludge are not measured.

Watanabe et al. (U.S. Pat. No. 5,324,43 1) disclose a method for controlling the activated sludge process that involves monitoring the particle size of coagulating microorganisms and the length of filamentous microorganisms in the sludge. This reference is limited by the use of complex measurement techniques that focus on predicting the occurrence of increases in sludge volume index or sludge bulking. The reference is further limited in that the settling, compacting and flocculating characteristics of the activated sludge are not measured.

Norcross (U.S. Pat. No. 5,421,995) discloses a sludge blanket-clarified liquid interface detector. This reference is limited in that only measurement of the depth of the sludge blanket in a decanter and measurement of the turbidity of decanter effluent in a sequencing-batch-reactor process are taught. The reference is further limited in that the settling, compacting and flocculating characteristics of the activated sludge are not measured.

Neilsen (U.S. Pat. No. 5,589,068) discloses a method for automatically controlling a wastewater purification plant that comprises measuring at least two system parameters, deriving a control parameter on the basis of the measurements and reference to at least two control functions, selecting a control action on the basis of the control parameter and implementing it. The method preferably incorporates an evaluation of the quality of the measurements that relies on the use of a mathematical model of the plant as described in Denmark Patent Application No. 1677/91. The reference is limited in that the settling, compacting and flocculating characteristics of the activated sludge are not measured.

Salem et al. (U.S. Pat. No. 5,601,704) discloses an automatic feedback control system for a water or wastewater treatment apparatus that incorporates a recirculating solids contact clarifier. The system maintains steady-state operation of the clarifier based on the accurate measurements of the concentration of suspended solids at designated locations in the clarifier. The reference is limited in that the settling, compacting and flocculating characteristics of the activated sludge are not measured.

Okey et al. (U.S. Pat. No. 5,733,456) discloses control of a water/wastewater treatment system based on sensing the oxidation reduction potential at various locations in the system. The reference is limited in that the settling, compacting and flocculating characteristics of the activated sludge are not measured.

The disclosures of a number of related art publications explain the activated sludge process and teach a variety of approaches to controlling the activated sludge process. The teachings of each of these publications is summarized below.

Wahlberg, E. J., in *Activated Sludge Bioflocculation: Measurement, Influencing Factors, and Physical Enhancement*, Ph.D. dissertation, Clemson University, May 1992, pp. ii–iv and 31–33, 46–51, 85–87, 104–112, 122–124, disclosed a batch flocculation testing procedure for characterizing activated sludge flocculation characteristics. Mixed liquor was collected from the aeration tank and placed in 2-liter square jars. The contents of each jar were gently stirred by a paddle on a 6-paddle Phipps and Bird stirrer at a rotation velocity of 37.5 rotations per minute for a flocculation time that varied from 0 to 64 minutes. After 30 minutes of settling, supernatant was removed from each jar with a j-shaped tube connected to a vacuum pump, and its turbidity was measured. Aeration tank MLSS and MLVSS concentrations as well as the total SS concentration of the supernatant were also measured, and the data were used to determine flocculation equation parameters. This reference is limited in that a conventional stirrer is used in data collection. It is further limited in that the settling and compacting characteristics of the activated sludge are not measured.

Wahlberg, E. J. and Parker, D. S. in Troubleshooting Activated Sludge Secondary Clarifier Performance with Simple Diagnostic Tests, Florida Water Resources Conference, Tampa, Fla., Aug. 28–31, 1994, pp. 1–7, teach how to determine whether flocculation problems or clarifier short-circuiting problems are causing elevated activated sludge secondary clarifier effluent suspended solids concentrations. Measurement of dispersed suspended solids concentration is accomplished by performing a suspended solids analysis on supernatant siphoned off of a sample of mixed liquor after settling in a 4.2 liter acrylic Kemmerer sampler for 30 minutes after collection (without flocculation). Measurement of flocculated suspended solids concentrations is accomplished by performing a suspended solids analysis on supernatant of a sample of mixed liquor after 30 minutes of slow-speed stirring followed by 30 minutes of settling in an undisclosed apparatus. This reference is limited in that a Kemmerer sampler is used in data collection. It is further limited in that the settling and compacting characteristics of the activated sludge are not measured.

Wahlberg, E. J., Keinath, T. M. and Parker, D. S. in Influence of Activated Sludge Flocculation Time on Secondary Clarification, *Water Environment Research*, 66(6), September/October 1994, pp. 779–786, disclosed an apparatus and method for performing a flocculation test. The test was the same as that described in the Wahlberg (1992) reference described above. This reference is limited in that a conventional stirrer is used in data collection. It is further limited in that the settling and compacting characteristics of the activated sludge are not measured.

Wahlberg, E. J., Bower J., Bittner, M. and Margolis, Z. in Al West Meets W. Deming: A Statistical Approach to the Control of the Activated Sludge Process, WEFTEC'94, Water Environment Federation 67th Annual Conference & Exposition, Chicago, Ill., Oct. 15–19, 1994, teach how to apply statistical process control principles to activated sludge process performance monitoring. In the first phase of the study, secondary clarifier effluent turbidity measurements were used as the control variable. In the second phase, the following activated sludge characteristics were measured in a 2-liter Mallory settlometer once per day: zone settling velocity (i.e., the slope of a best fit line through the 0, 5, 10 and 15 minute interface height-versus-time data) was used to characterize the rate of settling, 30-minute settled sludge volume was used to characterize the extent of sludge compaction, and supernatant turbidity after 30 minutes of settling was used to characterize the degree of flocculation. In the third phase of the study, the slope of the line between the 0 and 5 minute interface heights was used to characterize zone settling velocity and measurements were performed on a set of five samples, with each set of samples collected at four times during each day. It is important to note that no initial flocculation step (gentle stirring) was performed prior to settling. A limitation of this reference is that conventional settlometers and conventional settling test protocols are used in data collection. Another limitation is that "degree of flocculation" is incorrectly measured when the device and method disclosed in the reference are used as any flocs that exist in the aeration tank mixed liquor are broken up in the process of introducing the mixed liquor samples into the settlometers. This problem was unrecognized at this point in the development of the art. This reference thus teaches away from the previously published Wahlberg et al. references that teach how to perform other kinds of flocculation tests, which tests differ from the test disclosed herein. A further limitation is that no guidance is given as to how to use the collected data to implement specific control actions to optimize performance of the activated sludge process. The disclosure of this reference documents the status of the present inventor's search for a better activated sludge process control method, but also shows that as late as 1994 that search was not over.

Water Environment Federation, *Operation of Municipal Wastewater Treatment Plants*, Manual of Practice No. 11, Fifth Edition, 1996, Water Environment Federation: Alexandria, Va., pp. 571–613, 646–675 and 688–689, describes activated sludge process variations and discloses standard practices for controlling the process. Methods are presented for aeration and dissolved oxygen control, return activated sludge control and waste activated sludge control. A "sludge quality" method for return activated sludge control involves development of a mixed liquor settleability curve and measurement of return activated sludge and aeration tank mixed liquor concentrations with a centrifuge. A "sludge quality" method for waste activated sludge control involves measurement of a variety of factors, including secondary effluent quality, mixed liquor dissolved oxygen concentration, oxygen uptake rate or respiration rate, mixed liquor, return activated sludge and waste activated sludge concentrations with a centrifuge and settled sludge concentration with a settlometer, typically at 5, 10, 15, 20, 25, 30, 40, 50 and 60 minutes with no flocculation. It is significant that this standard industry reference, which was authored by wastewater process control experts and published as late as 1996, teaches away from the devices and methods disclosed herein.

Wahlberg, E. J., Crowley, J. P., Bower, J., Bittner, M. and Margolis, Z. in Why the Activated Sludge Process Is So Hard to Operate: Modeling Brings New Light to Operations, WEFTEC'96, Water Environment Federation 69th Annual Conference & Exposition, Dallas, Tex., Oct. 5–9, 1996, disclose the conflicts that arise when using constant SRT, constant MLVSS and constant F:M ratio in waste activated sludge flow rate control strategies. A "more sludge quality based approach to control" of the activated sludge process is suggested but the reference is limited in that such an approach is not disclosed in it.

The above review of the background art reveals that no combination of references teach the invention disclosed herein. Even those references that suggest the use of "sludge quality" approaches to activated sludge process optimization do not teach the use of simple devices that allow for measurement of all of the important dimensions of sludge quality as required by this invention. No combination of references teach accurate measurement of the settling, compacting and flocculating characteristics of the activated sludge and/or use of such data for activated sludge process control. Even the references authored or coauthored by the inventor of the invention disclosed herein merely illustrate his up-until-now unsuccessful search for an elegant solution to the problem of activated sludge process optimization.

BRIEF SUMMARY OF THE INVENTION

The purpose of the invention is to provide means for controlling and optimizing activated sludge process performance. The invention gives wastewater treatment plant operators a new tool for making the process-control decisions that affect activated sludge process performance. The invention provides an apparatus and a procedure for measuring a sludge's settling, compacting, and flocculating characteristics. Moreover, the invention provides a technique for controlling the activated sludge process using the apparatus and procedure.

The invention is an apparatus and method for optimizing activated sludge process performance. The apparatus comprises means for measuring the following characteristics of an activated sludge: settling, compacting and flocculating. In a preferred embodiment, the apparatus comprises a motor platform, at least three (preferably four), vertically-oriented stator/legs connected to and extending below said motor platform, a motor attached to said motor platform, a vertically-oriented shaft extending below said motor, said shaft having a length that is less than the length of said statorAegs and having a mixer blade attached thereto. The apparatus is configured so that the stator/legs fit within a cylindrical container holding a sample of activated sludge mixed liquor with the bottoms of the stator/legs resting on the bottom of said container when the apparatus is in use. When flocculation is complete or when the apparatus is not in use, it is removed from the container and may be stored in the same orientation on the surface that the container is resting on by resting the bottoms of the stator/legs on the surface. The apparatus may also comprise the container, which container has an effective volume of about 2 liters. The container is fitted with a sampling port on its side through which a sample of the liquid near the top of the container may be removed. In a preferred embodiment, this sampling port is positioned at approximately one quarter of the height of the sample down from the water surface. In an alternative embodiment, a timer is used to control the length of time that each sample is stirred, settled and sampled.

In use, this embodiment is capable of mixing the sample and of being used to measure the settling character of the sludge, to measure the compacting character of the sludge, and to measure the flocculating character of the sludge. Mixing is accomplished using the motor to rotate the shaft at approximately 60 revolutions per minute (rpm) for approximately 30 minutes. While the appropriate rotational speed and duration can vary within the ranges 50 and 70 rpm and approximately 5–60 minutes for any particular sludge, it is important that essentially the same rotational speed and duration be used between tests. The settling character of the sludge is quantified by measuring the distance to which the interface between the solids and the liquids in the sample drops by approximately five minutes after stirring has stopped. Alternatively, the volume occupied by the settled solids approximately five minutes after stirring has stopped is used. The compacting character of the sludge is quantified by measuring the distance to which the interface between the solids and the liquid in the sample drops by approximately 30 minutes after stirring has stopped. Alternatively, the volume occupied by the settled solids approximately 30 minutes after stirring has stopped is measured and used. The flocculating characteristic is quantified by removing a sample of the supernatant liquid and measuring its turbidity or total suspended solids concentration (Water Environment Federation, *Standard Methods for the Examination of Water and Wastewater,* 20th Edition, 1998).

Another embodiment of the invention comprises the use of a Mallory settlometer fitted with stators and a stirring device to quantify the settling, compacting and flocculating characteristics of an activated sludge. The supernatant sample after stirring and settling can be obtained either from a sampling port tapped into the side of the settlometer or by withdrawing supernatant from the top of the settlometer using a siphon or other vacuum device. First, a two-liter (L) representative sample of activated sludge is removed from an aeration tank and placed in the modified settlometer. After the sample is flocculated, the interface between the liquid and the solids that comprise the sludge (termed the "liquid/ solids interface") is considered to be at the top of the sludge sample.

The settling characteristic of the sludge is quantified by stirring the sludge for approximately 30 minutes at about 60 rpm, then ceasing the stirring and measuring the linear distance the solids/liquid interface has dropped (settled) in a given time, preferably approximately five minutes after the stirring has stopped. The linear distance can be divided by the settling time of five minutes to calculate the settling velocity ($V_s$) of the sludge. Alternatively, the volume occupied by the settled solids approximately five minutes after stirring has stopped is used.

The compacting characteristic of the sludge is quantified by measuring the degree to which the sludge has compacted in a given time, preferably approximately 30 minutes after the stirring has stopped. The linear distance that the solids/ liquid interface has dropped after stirring has stopped is divided by the depth of the sludge sample (the original height of the solids/liquid interface measured from the bottom of the settlometer) to produce a proportion or percentage compaction. Alternatively, the volume occupied by the settled solids approximately 30 minutes after stirring has stopped is measured and used.

The flocculating characteristic of the sludge is quantified by measuring the turbidity of the liquid present at the top of the settlometer at a given time, preferably approximately 30 minutes after stirring has stopped. To make the measurement, a sample of liquid is removed from the settlometer 30 minutes after stirring has stopped and placed in a turbidimeter (e.g., a Nessler turbidimeter) for a determination of its turbidity (e.g., in Nephlometeric turbidity units or NTUS). Alternatively, this sample can be analyzed for its total suspended solids concentration (Water Environment Federation, *Standard Methods for the Examination of Water and Wastewater,* 20th Edition, 1998).

In yet another embodiment of the invention, the apparatus comprises means for removing a representative aliquot of activated sludge from an aeration tank or basin (preferably near the exit end of the tank or basin) and a reactor that provides means for mixing the sample, means for measuring the settling character of the sludge, means for measuring the compacting character of the sludge and means for measuring the flocculating character of the sludge. In one preferred embodiment, the aliquot of activated sludge is removed from the aeration tank by suction (i.e., it does not pass through a pump) to minimize uncontrolled disruption of its character. Suction may be provided by a pump located downstream of the reactor.

In this embodiment, mixing is provided by configuring the reactor so that eddy currents are caused when a shaft fitted with a mixing blade or paddle is rotated in the container. This may be accomplished by configuring the reactor so that it is non-circular (e.g., square) in horizontal cross section or by providing at least two stators that disrupt the circular motion of the aliquot when a motor-driven shaft having a mixing blade or paddle rotates in the reactor.

In this embodiment, means for measuring the settling character of the sludge is provided by fitting the apparatus with a means for measuring the distance by which the solids/liquid interface has dropped in a specified period of time after stirring has ceased, preferably in 5 or 10 minutes. If the walls of the reactor are transparent, optic means can be used, e.g., a light source on one side of the reactor and a vertically-oriented series of photocells on the other side to determine the height of the solids/liquid interface. Alternatively, a turbidity sensor is lowered into the reactor until a large increase in turbidity is sensed, indicating the level of the solids/liquid interface or an ultrasonic probe is used to sense the level of the solids/liquid interface.

In this embodiment, means for measuring the compacting character of the sludge is provided by fitting the apparatus with a means for measuring the distance by which the solids/liquid interface has dropped in a second specified period of time after stirring has ceased, preferably in 30 minutes. In a preferred embodiment, the same means is used to measure this distance as is used to measure the settling character of the sludge.

In this embodiment, means for measuring the flocculating character of the sludge is provided by fitting the apparatus with means to measure the turbidity of the liquid that has separated from the sludge during settling. In a preferred embodiment, this is accomplished by slowly (so as not to disturb the settled solids) removing a sample of the liquid from the top of the reactor and measuring its turbidity in a turbidimeter.

Still another embodiment of the invention comprises collection of a first group of data on the settling, compacting and flocculating characteristics of an activated sludge at a first point in time and then collection of a second group of data on the settling, compacting and flocculating characteristics of an activated sludge at a second, subsequent point in time. The first group of data are compared to the second group of data to determine whether the settling, compacting and/or flocculating characteristic(s) of the sludge has changed significantly, and, if so, in which direction (e.g., increase or decrease). A knowledgebase of rules (preferably in the form, IF <predicate>THEN<consequent>) concerning how to modify the aeration rate, return activated sludge flow rate and the waste activated sludge flow rate depending on whether sludge settling, compacting and flocculating characteristics have changed and, if so, in which direction, is then accessed. An inference is made as to the activated sludge process operating strategy that is most likely to optimize the performance of the process by processing said rules. The operational strategy is then implemented to control the activated sludge process and produce the best quality effluent.

In a further embodiment, the invention is an activated sludge treatment plant controlled using the process disclosed herein. In a preferred embodiment, the activated sludge treatment plant includes an influent pumping station, a headworks, primary sedimentation tank(s), activated sludge aeration basin(s), secondary clarifier(s), flow-adjustable RAS pump(s), flow-adjustable WAS pump(s), flow-adjustable blower(s), disinfection facilities, sludge stabilization units and process control features.

In broad terms, a preferred embodiment of the apparatus is comprised of means for measuring, at a plurality of points in time, the settling character of an activated sludge, the compacting character of an activated sludge and the flocculating character of an activated sludge. Other embodiments of the invention further comprise means for processing the measurements so produced by, for example, statistical process control techniques, to produce appropriate operational strategies for activated sludge process control and/or troubleshooting. Yet other embodiments of the invention further comprise a wastewater treatment plant being operated as disclosed herein.

In broad terms, a preferred embodiment of the method is comprised of the following steps: measuring, at a plurality of points in time, the settling character of an activated sludge, the compacting character of an activated sludge and the flocculating character of an activated sludge and processing the measurements so produced using a knowledgebase or rule set to produce appropriate operational strategies for activated sludge process control. Other embodiments of the invention involve a rule set for selection of optimum activated sludge process control strategies. Other embodiments involve computer control of an activated sludge process based on said strategies. Other embodiments involve troubleshooting of an activated sludge process based on said strategies.

The present invention calls for quantification of the inherent variability in the activated sludge process before taking control actions. The most likely result of not quantifying this variability is "over control;" that is, making a process control change when no change is warranted. This often occurs when a change in the quality characteristic (i.e., a measurable performance variable) occurs, but that change is completely within the normal variability of the system.

The present invention is based on the recognition that it is inappropriate to measure the quality of the end product without measuring the quality of the intervening steps taken to make that product (e.g., sludge quality) and expect to consistently meet performance specifications. It recognizes that it is inappropriate, therefore, for an operator of an activated sludge plant to base control decisions on final effluent quality as is often done today. This disclosure illustrates that, in fact, controlling the quality of the activated sludge—ensuring a sludge is grown that settles, compacts, and flocculates well—is absolutely key to successful activated sludge operation. Unfortunately, an easily-performed but meaningful method of sludge quality measurement does not exist. The invention described herein is designed to address this void. In addition, the invention provides that the tests disclosed herein be conducted in such a way that the data provide a means for quantifying system (along with sample and analytical error, although these tests attempt to minimize these errors) variability. It is with an understanding of this variability that actual changes in the process can be seen and responded to.

One advantage of the invention is that it provides a simple means for measuring the settling character of an activated sludge, the compacting character of an activated sludge and the flocculating character of an activated sludge, these characteristics being tantamount to the successful performance of the activated sludge process. These characteristics of an activated sludge can have a huge impact on how an activated sludge system will perform, how large a plant must be built, and/or what the capacity of an existing plant is. Yet, before this invention, no one had a way of measuring all of these very important sludge quality characteristics. Another advantage of the invention is that it provides a rational approach to activated sludge plant operation. Yet another advantage of the invention is that it can be used by wastewater treatment plant operators to determine whether a change should be made in the operation of an activated sludge process, and, if a change is appropriate, the nature and extent of the change. A further advantage of the invention is that it provides a wastewater treatment plant that operates as it was intended to operate during its design and when expansion of that design is necessary. Another advantage of the invention is that it allows measurement of the flocculating character of an activated sludge to be performed as part of a test that most operators already do: the settlometer test. A further advantage of the invention is that it incorporates the use of statistical process control to quantify the variability of control parameters in a way that prevents over control of the activated sludge process.

The art of activated sludge process control has not changed for decades. The short schools, correspondence courses, associate degrees and certification exams teach the same approach: kinetic control. The present invention represents a paradigm shift in at least two significant ways: focusing on sludge quality characteristics and quantifying their variability. With this approach, a goal that has eluded operators for decades can be achieved: activated sludge process optimization.

Further aspects of the invention will become apparent from consideration of the drawings and the ensuing description of preferred embodiments of the invention. A person skilled in the art will realize that other embodiments of the invention are possible and that the details of the invention can be modified in a number of respects, all without departing from the inventive concept. Thus, the following drawings and description are to be regarded as illustrative in nature and not restrictive.

BRIEF DESCRIPTION OF THE SEVERAL VIEWS OF THE DRAWINGS

The features of the invention will be better understood by reference to the accompanying drawings which illustrate presently preferred embodiments of the invention. In the drawings.

Figure 1:
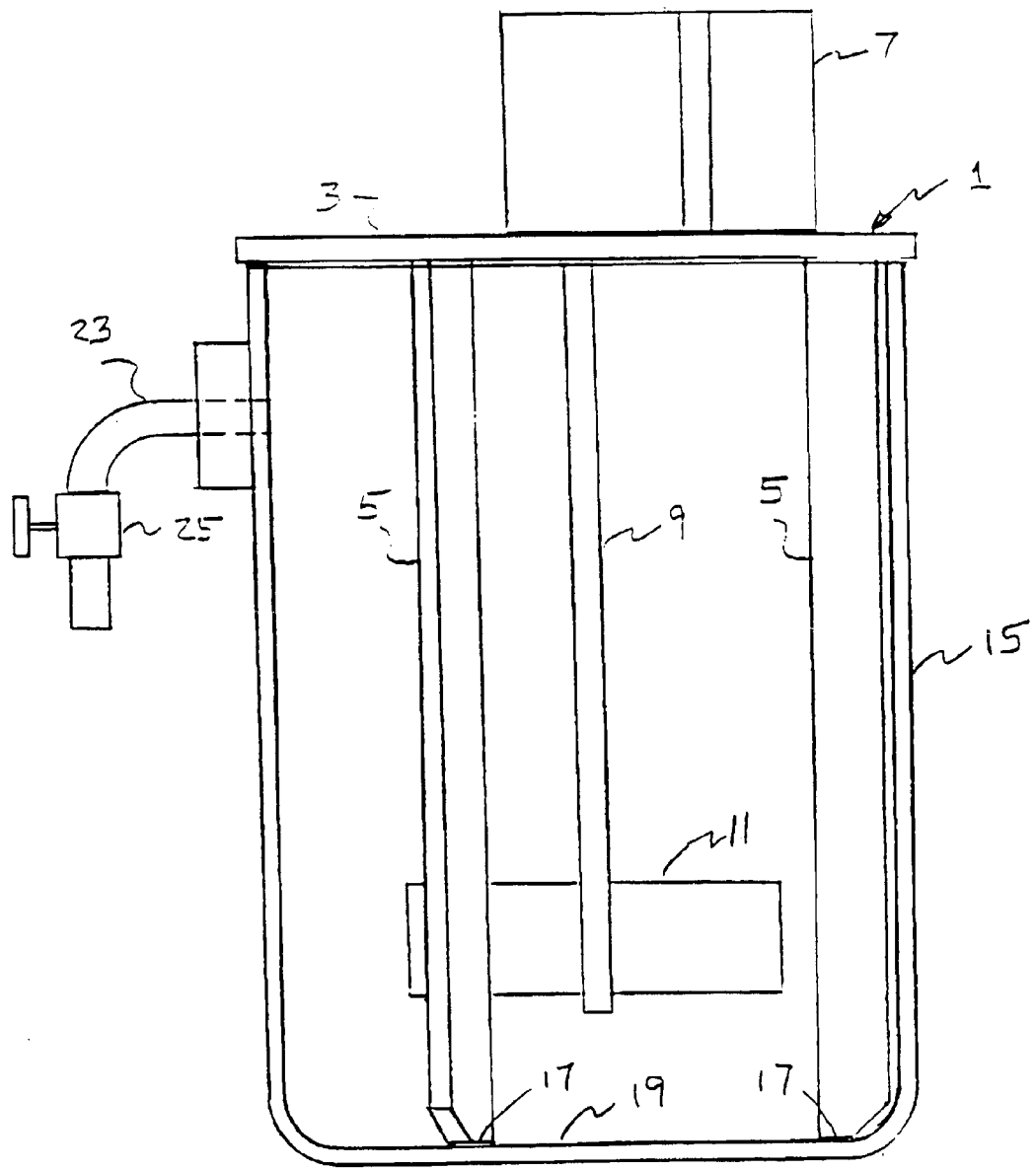
FIG. 1 is an elevation view of a preferred embodiment of the invention.

The following reference numerals are used to indicate the parts and environment of the invention on the drawings:

Apparatus 1
Motor platform 3
Stators/legs 5
Motor 7
Shaft 9
Mixer blade 11
Settling container 15
Stator/leg bottoms or feet 17
Container bottom 19
Supernatant sampling port 23
Supernatant sampling port valve 25
System 31
Aeration basin 33
Blower(s) 35
Return activated sludge pump(s) 37
Secondary, or final, clarifier 39
Waste activated sludge pump(s) 43
Sludge quality sensor 47
Pump 49
Pump 50
Container 51
Stators 53
Motor-mounting plate 55
Motor 57
Shaft 59
Mixer blade 61
Sludge blanket depth sensor 63
Turbidimeter 65
Drain 65
Valve 66
Computer 67
Sensing and control circuit 68
Processor 69
Monitor 71

DETAILED DESCRIPTION OF THE INVENTION

Referring to FIG. 1, a preferred embodiment of apparatus 1 is illustrated. In this embodiment, apparatus 1 comprises motor platform 3, at least three (preferably four) vertically-oriented stators/legs 5 connected to and extending below motor platform 3, motor 7 attached to motor platform 3, vertically-oriented shaft 9 extending below motor 7, said shaft 9 having a length that is less than the length of said stators/legs 5 and having mixer blade 11 attached thereto. Apparatus 1 is configured so that stators/legs 5 fit within the sidewalls of cylindrical settling container 15 holding a sample of activated sludge mixed liquor with stator/leg bottoms or feet 17 resting on container bottom 19 when the apparatus is in use. When apparatus 1 is not in use or when flocculation is complete, it is removed from container 15 and may be stored in the same orientation on the surface that the container is resting on by resting bottoms 17 of stator/legs 5 on the surface. Apparatus 1 may also comprise container 15, which container has an effective volume of about 2 liters. Container 15 is fitted with supernatant sampling port 23 on its side through which a sample of the liquid near the top of container 15 may be removed when supernatant port valve 25 is opened. Sampling port 23 is preferably located about two-thirds up the side of container 15. Alternatively, supernatant samples may be collected through a siphon, or other vacuum device, placed over the side of container 15.

In use, this embodiment is capable of stirring a sample of activated sludge collected from an activated sludge process and of being used to measure the settling character of the sludge, to measure the compacting character of the sludge and to measure the flocculating character of the sludge. Stirring is accomplished by causing electric motor 7 to rotate shaft 9 at approximately 60 revolutions per minute (rpm) for approximately 30 minutes. The settling character of the sludge is quantified by measuring (with a ruler or other means) the distance the interface between the solids and the liquid in the sample drops in approximately five minutes after stirring has stopped. In an alternative embodiment, the settling character of the sludge is quantified by measuring the volume occupied by the settled solids approximately five minutes after stirring has stopped. The compacting character of the sludge is quantified by measuring the distance the interface between the solids and the liquid in the sample drops approximately 30 minutes after stirring has stopped. In an alternative embodiment, the compacting character of the sludge is quantified by measuring the volume occupied by the settled solids approximately 30 minutes after stirring has stopped. The flocculating characteristic is quantified by removing a sample of the liquid after approximately 30 minutes of settling by opening valve 25 on sampling port 23 and by measuring the turbidity or total suspended solids concentration of the supernatant sample.

Figure 2:
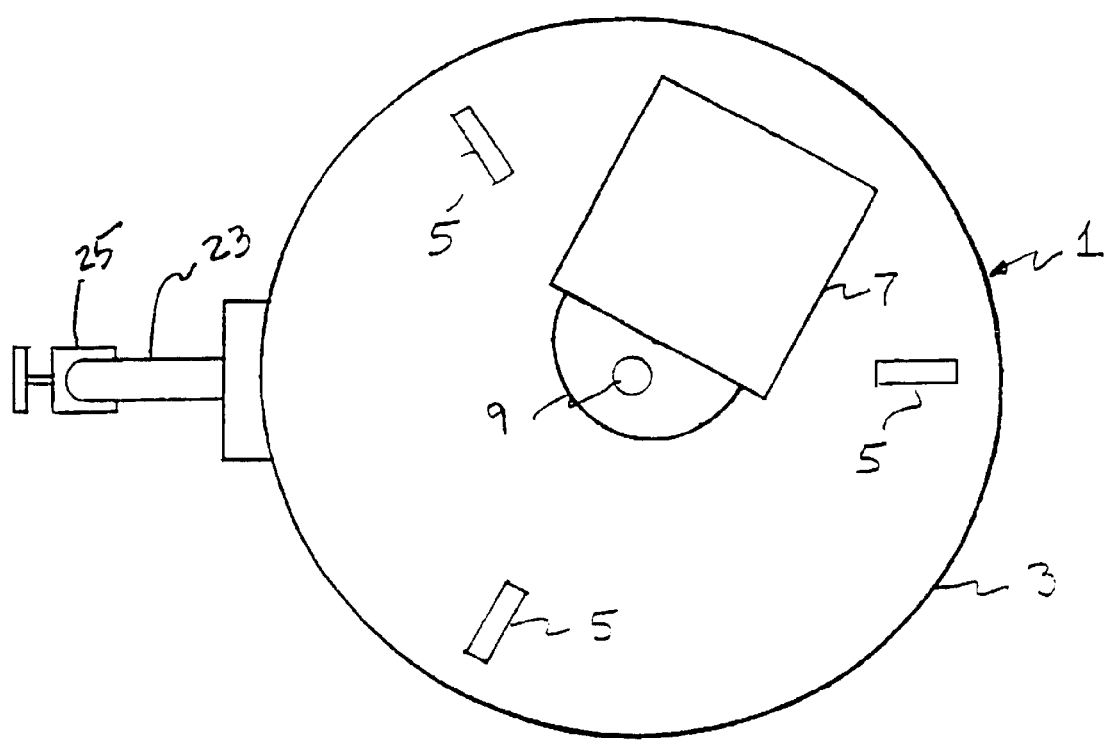
FIG. 2 is a top view of a preferred embodiment of the invention.

Referring to FIG. 2, a top view of apparatus 1 is presented. Motor 5 is attached to the top of motor platform 3 and stators/legs 5 are attached to the bottom of motor platform 3. In this embodiment, three stators/legs 5 are provided and are located about 120 degrees apart. In an alternative embodiment, four stators/legs 5 are provided and are located about 90 degrees apart. Shaft 9 is driven by motor 7 and is located in the middle of motor platform 3.

Figure 3:
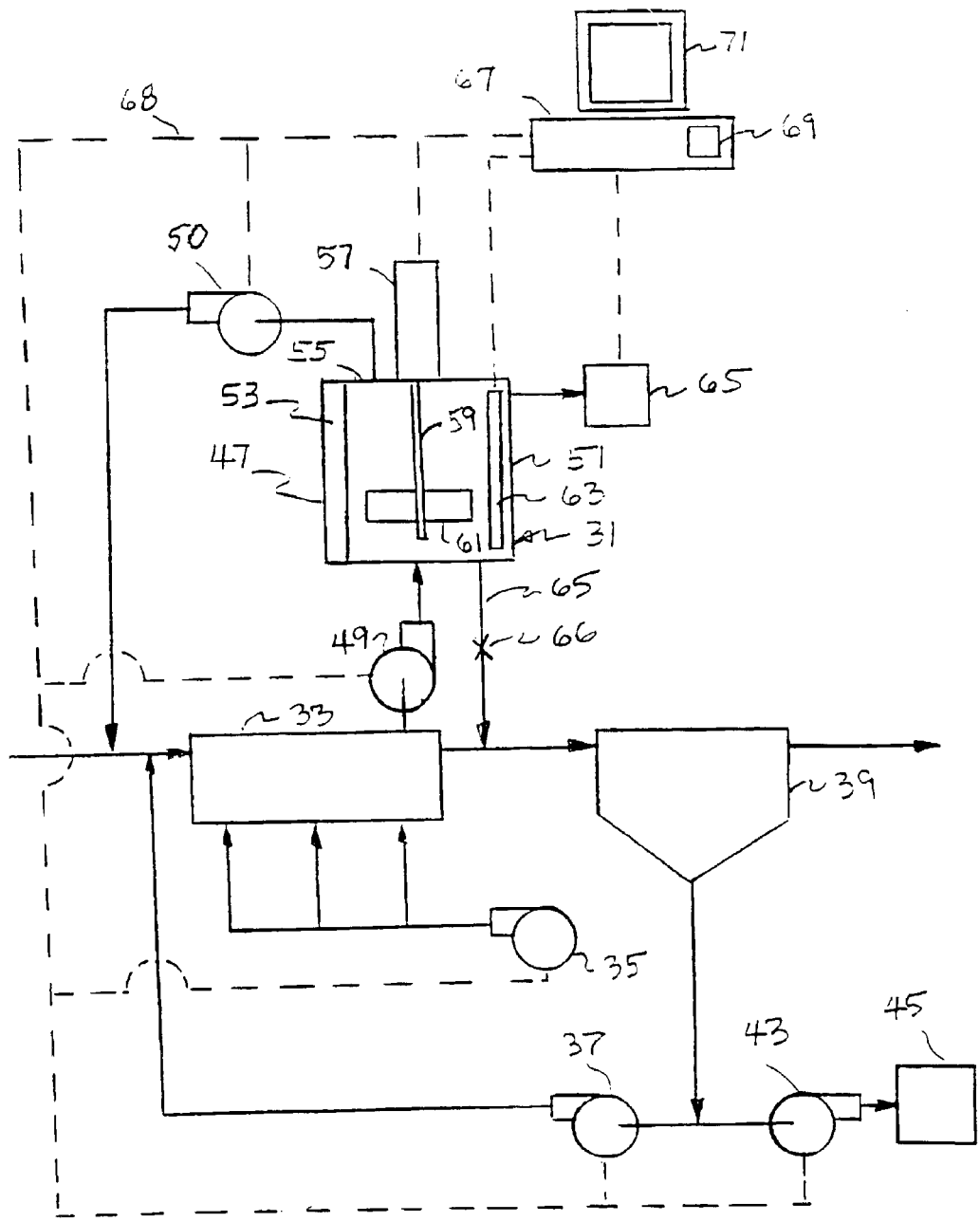
FIG. 3 is a schematic diagram of another preferred embodiment of the invention.

Referring to FIG. 3, a schematic diagram of system 31 is illustrated. Wastewater is delivered to a wastewater treatment plant and undergoes influent pumping, screening and primary sedimentation before being introduced to aeration basin 33. In an alternative embodiment, primary sedimentation does not occur. Air or oxygen is introduced to aeration basin 33 by means of blower(s) 35. As it is introduced to aeration basin 33, the wastewater is mixed with return activated sludge that is delivered to the aeration basin 33 by return activated sludge pump(s) 37. Mixed liquor produced in aeration basin 33 is introduced to secondary, or final, clarifier 39. Return activated sludge pump 37 removes settled sludge from secondary, or final, clarifier 39. A portion of the settled sludge is removed from the system ("wasted") by means of waste activated sludge pump(s) 43 and is preferably discharged to sludge stabilization operation 45. Alternatively, mixed liquor can be wasted directly from aeration basin 33.

At regular intervals, a sample of the contents of aeration basin 33 (a sample of activated sludge mixed liquor) is withdrawn from aeration basin 33 and placed in sludge quality sensor 47 by pump 49 for sensing of the sludge's settling, compacting and flocculating characteristics.

Sludge quality sensor 47 comprises container 51, stators 53, motor-mounting plate 55, motor 57, shaft 59, mixer blade 61, sludge blanket depth sensor 63 and turbidimeter 65. In a preferred embodiment, sludge quality sensor 47 is automatically emptied and flushed with water before each new sample of activated sludge mixed liquor is taken. Sludge quality sensor 47 is drained through drain 65 controlled by valve 66. Alternatively, sludge quality sensor 47 is emptied by action of pump 50.

The activated sludge process and, preferably, other unit operations of the wastewater treatment plant are controlled by computer 67. Control of the activated sludge process is accomplished by means of sensing and control circuit 68, based on processing by processor 69 of input signals from sludge quality sensor 47. System status is displayed on monitor 71.

In operation, when a sample of activated sludge is collected and introduced into sludge quality sensor 47, the sample is stirred for 30 minutes and then stirring is stopped and the sample is allowed to settle. The settling character of the sludge is quantified by using sludge blanket depth sensor 63 to measure the distance the interface between and solids 63 and the liquids in the sample drops approximately five minutes after stirring has stopped. In an alternative embodiment, the settling character of the sludge is quantified by measuring the volume occupied by the settled solids approximately five minutes after stirring has stopped. The compacting character of the sludge is quantified using sludge blanket depth sensor 63 to measure the distance the interface between the solids and the liquids in the sample drops approximately 30 minutes after stirring has stopped. In an alternative embodiment, the compacting character of the sludge is quantified by measuring the volume occupied by the settled solids approximately 30 minutes after stirring has stopped. The flocculating characteristic is quantified by removing a sample of the supernatant and by measuring its turbidity by means of turbidimeter 65.

The output signals of sludge blanket depth sensor 63 and turbidimeter 65 are transmitted to computer 67 and are processed by processor 69 as data. In some embodiments, said output signals are displayed on monitor 71. In some embodiments, the instructions used to operate processor 69 in computer 67 are accessed on a storage medium such as a compact disk.

Each previous group of data are compared to a subsequent group of data to determine whether the settling, compacting and/or flocculating characteristic(s) of the sludge has changed significantly, and, if so, in which direction (e.g., increase or decrease). In a preferred embodiment, a statistical process-, or a statistical quality-, control approach is used to determine whether measured changes in average measurements are statistically significant to prevent overreaction to apparent but insignificant changes.

A knowledgebase of rules in the form (IF<predicate>THEN<consequent>) concerning how to modify the aeration rate, return activated sludge flow rate and the waste activated sludge flow rate depending on whether sludge settling, compacting and flocculating characteristics have changed and, if so, in which direction, is then accessed by processor 69. An inference is made (preferably by an expert system engine residing in processor 69) as to the activated sludge process operating strategy that is most likely to optimize the performance of the process by processing said rules, preferably by means of an expert system. The operational strategy is then implemented to control the activated sludge process. In order to implement the strategy, computer 67 sends signals (via sensing and control circuit 68) to the drivers of aeration blower(s) 35, return activated sludge pump(s) 37 and/or waste activated sludge pump 43 to maintain, increase or decrease their outputs. In a preferred embodiment, flow meters are provided on aeration air, RAS and WAS discharge pipelines to allow sensing of changes in the actual flow rates occurring in those lines by means of sensing and control circuit 68.

In a preferred embodiment, the operational strategy is communicated by computer 67 to the wastewater treatment plant operator via monitor 71. The wastewater treatment plant operator can override implementation of the strategy and/or modify it.

In a preferred embodiment, a statistical process control approach is used. Due to ever-changing flows and loads, the performance of wastewater treatment plants is highly variable. Unlike other treatment processes, however, the activated sludge process is characterized by a relatively high degree of control. In all activated sludge systems, the three primary control variables are: (1) the air flow rate, (2) the return activated sludge (RAS) flow rate, and (3) the waste activated sludge (WAS) flow rate. Other control variables available to some, but not all, activated sludge plants include: step-feed location, use of oxic, anoxic and anaerobic zones, nutrient addition, pH control, and temperature control. The last three of these generally are needed only in some industrial waste treatment systems.

In the present invention, sludge quality variability is quantified using statistical process control (also known as statistical quality control) techniques. These techniques were originally developed in the 1920s by Walter Shewhart of Bell Laboratories. These techniques involve the development of control charts, or process learning charts. Although a number of different charts have been advanced over the years, the most appropriate charts to use for the data collected using the invention disclosed herein are the X-bar and the S, or R, charts. With a system where the quality characteristics is variable, such as the apparatus described herein, it is desired (as described above) to control both the mean value and its variability. Controlling the process average requires the use of the X-bar chart; controlling the process variability requires the use either a chart of standard deviations (i.e., the S chart) or a chart of ranges (i.e., the R chart). Examples of the use of these control charts have been published (Montgomery, D. C., *Statistical Quality Control*, John Wiley & Sons, Inc., New York, 1995, p. 107).

With the present invention, rather than plotting single observations, from which rational decisions cannot be made, multiple observations are collected over time and subgrouped when using statistical process control. The average and standard deviation, or range, of the subgroups are calculated and plotted on the X-bar and S, or R, charts, respectively. Three control lines also are plotted on each chart: the central control line (CCL), the upper control limit (UCL), and the lower control limit (LCL). These lines are plotted based on estimates of the population (rather than the subgroup) mean and variance and the probability of making type I and type II errors (i.e., concluding statistical control does not exist when it does and concluding statistical control does exist when it does not). Estimates of the population variance depend on the size of the sample, as presented in any book on statistical process, or quality, control. Thus, the design of control charts requires that the control limits, sample size, and sample frequency be selected. Sample size and frequency fall into the notion of subgrouping. As described by Shewhatt, a rational subgrouping strategy is one in which the chance for measuring differences between subgroups is maximized, while the chance for measuring differences within each subgroup is minimized. Thus, because the magnitude of inherent variability is different for each wastewater, an all-encompassing sampling design cannot be given.

A preferred approach to use of these techniques using the apparatus described herein is as follows:

1. Assume, for example, at activated sludge wastewater treatment plant A (WWT P-A) three shifts are operated: shift 1–7:00 a.m. to 3:30 p.m., shift 2–3:00 p.m. to 11:30 p.m., and shift 3–11:00 p.m. to 7:30 a.m.
2. At 8:00 a.m. (shift 1), 4:00 p.m. (shift 2) and 12:00 midnight (shift 3), the apparatus described herein (termed the Wahlometer™) is used to measure sludge quality; that is, sludge settling is quantified by the 5-minute settled sludge volume (SSV5), sludge compaction is quantified by the 30-minute settled volume (SSV30), and sludge flocculation is quantified by the supernatant turbidity (TURB) or total suspended solids (TSS) after 30 minutes settling after 30 minutes of flocculation.

For each of the quality characteristics (i.e., SSV5, SSV30, and TSS or TURB), the average and range are calculated from the three observations made each day and plotted on their respective chart (the subgrouping sample size, therefore, is three). X-bar and R charts are maintained for each quality characteristic; therefore, six charts are maintained.

4. After the $20^{th}$ day, estimates of the population mean ($\mu$) and standard deviation ($\sigma$) are made.
5. CCLs, UCLs, and LCLs are plotted on the six charts using the values determined in step 4.
6. If all the averages and ranges collected over the 20 days fall within the upper and lower control limits, the system is considered to be in a state of statistical control; that is, only unassignable (i.e., uncontrollable) sources of variation prevail. The CCLs, UCLs, and LCLs can continue to be used to monitor the state of statistical control of future data points (i.e., averages and ranges).
7. If any of the averages or ranges for the first 20 days fall outside the control limits, they should be investigated. If any of these out-of-control points can be explained by the occurrence of assignable causes of variation, they should be discarded and new estimates of $\mu$ and $\sigma$ are calculated and new values for the CCLs, UCLs, and LCLs determined. After this investigation, the modified CCLs, UCLs, and LCLs then can be used to monitor the state of statistical control of future data points.
8. The values determined in steps 4 or 7 are considered to be trial values. The calculations for determining the CCLs, UCLs, and LCLs should be fine tuned as more data are collected.
9. Once the CCLs, UCLs, and LCLs for the three sludge quality characteristics are set, sampling, calculating, and plotting continue in exactly the same manner. The control charts are then used to maintain a state of statistical control. If the future data points plotted on the control charts display a random pattern about the CCLs and stay within the control limits, the system is behaving as originally measured and no corrective actions should be taken. A data point plotting outside the control limits indicates the occurrence of an assignable cause of variation. This result would mobilize the operations staff to determine the cause of this variation, paying particular attention to the operation of the three primary control points in an activated sludge process, the air, RAS, and WAS flow rates. Also, if the plotted data points exhibit a nonrandom or systematic pattern (e.g., seven consecutive data points moving in the same direction, an inordinate number of data points on one side of the CCL, etc.), the system may be or is tending to be out of control and corrective action should be taken in accordance with a knowledgebase of rules that relate sludge quality changes to control actions.

While it is the case that a somewhat different knowledgebase of rules will be appropriate for each wastewater treatment plant, some rules are likely to be consistent across a wide spectrum of plant types. Examples of rules that are generally applicable are given in Table 1. The rules given in Table 1 are refined as more data are obtained using the invention.

TABLE 1

Examples of Rules that Relate Sludge Quality Changes to Control Actions

| Observations | | | | Process control change(s): | | |
|---|---|---|---|---|---|---|
| SSV5 | SSV30 | TURB | Comments | RAS | WAS | Air |
| ↔ | ↔ | ↔ | No changes, leave the system alone | Nc | Nc | Nc |
| ↔ | ↔ | ↓ | "Free" effluent improvement; if long-lived, adjust control limits on charts accordingly | Nc | Nc | Nc |
| ↔ | ↔ | ↑ | Deflocculation due to inadequate air | Nc | Nc | Incr |
| ↔ | ↓ | ↔ | Possible loss of aeration basin solids due to plugged RAS line | Chk | Nc | Nc |
| ↔ | ↓ | ↓ | Check RAS rate, otherwise leave system alone; if long-lived, adjust control limits on charts accordingly | Chk | Nc | Nc |
| ↔ | ↓ | ↑ | Either over or under aeration; check aeration rate | Nc | Nc | Chk |
| ↔ | ↑ | ↔ | Early filamentous organism growth in sludge, confirm with microscopic examination; depending on filament, make appropriate changes | Nc/d | Nc/d | Nc/d |
| ↔ | ↑ | ↓ | No changes, leave the system alone | Nc | Nc | Nc |
| ↔ | ↑ | ↑ | No changes, leave the system alone | Nc | Nc | Nc |
| ↓ | ↔ | ↔ | Unexplained settling velocity decrease, perhaps from influent constituent; if long-lived, adjust control limits on charts accordingly | Nc | Nc | Nc |
| ↓ | ↔ | ↓ | No changes, leave the system alone | Nc | Nc | Nc |
| ↓ | ↔ | ↑ | No changes, leave the system alone | Nc | Nc | Nc |
| ↓ | ↓ | ↔ | No changes, leave the system alone | Nc | Nc | Nc |
| ↓ | ↓ | ↓ | No changes, leave the system alone | Nc | Nc | Nc |
| ↓ | ↓ | ↑ | No changes, leave the system alone | Nc | Nc | Nc |
| ↓ | ↑ | ↔ | Excessive solids in system | Nc | Incr | Nc |
| ↓ | ↑ | ↓ | Filamentous organism growth | Incr | Incr | (Incr) |
| ↓ | ↑ | ↑ | No changes, leave the system alone | Nc | Nc | Nc |
| ↑ | ↔ | ↔ | Unexplained settling velocity increase, perhaps from influent constituent | Nc | Nc | Nc |
| ↑ | ↔ | ↓ | No changes, leave the system alone | Nc | Nc | Nc |
| ↑ | ↔ | ↑ | Unexplained settling velocity increase resulting in improved flocculation, perhaps from influent constituent | Nc | Nc | Nc |
| ↑ | ↓ | ↔ | No changes, leave the system alone | Nc | Nc | Nc |
| ↑ | ↓ | ↓ | Solids accumulation in secondary clarifier(s) with desirable result | Incr | Incr | Nc |
| ↑ | ↓ | ↑ | No changes, leave the system alone | Nc | Nc | Nc |
| ↑ | ↑ | ↔ | No changes, leave the system alone | Nc | Nc | Nc |
| ↑ | ↑ | ↓ | No changes, leave the system alone | Nc | Nc | Nc |
| ↑ | ↑ | ↑ | No changes, leave the system alone | Nc | Nc | Nc |

Figure 4:
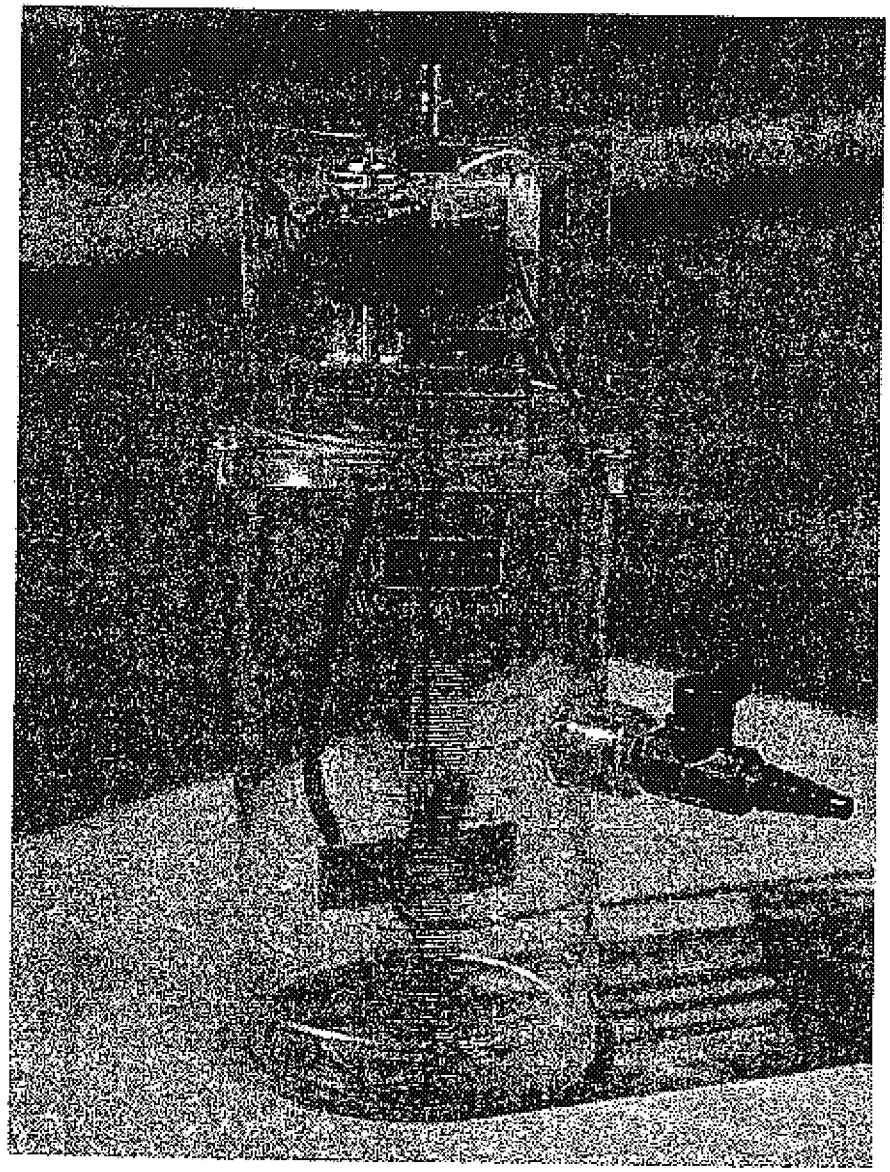
FIG. 4 is a photograph of a commercial embodiment of the invention.

Notes:
Nc = no change;
Incr = increase;
Decr = decrease;
Nc/d = no change, depends on outcome of additional testing;
↑ = increase in quality characteristic;
↓ = decrease in quality characteristic;
↔ = no change in quality characteristic;

A photograph of a commercial version of apparatus 1 is presented in FIG. 4. The apparatus and method described herein were implemented at the Empire Wastewater Treatment Plant (Empire) in Farmington, Minnesota, in late May 1999. The plant is one of nine plants owned and operated by the Metropolitan Council Environmental Services serving the greater Twin Cities metropolitan area. Empire treats 12 million gallons per day of wastewater in a two-stage, carbonaceous removal and nitrification, activated sludge system. The apparatus and method were used on both stages.

As an indication of the results achieved by the apparatus and method, the effluent quality from the second stage activated sludge system at Empire has been so consistently good, after nearly a year, that the dual media filters downstream of the activated sludge systems are being considered for discontinuation. Ironically, the filters were originally constructed and placed in service to lower the variability of the quality of the effluent discharged from the facility.

Many variations of the invention will occur to those skilled in the art. Some variations include manual measurement of sludge quality characteristics. Other variations call for automating such measurements. Other variations involve using the measurements to determine when taking no action will improve process performance. All such variations are intended to be within the scope and spirit of the invention.

I claim:

1. A device for measuring the quality of a sample of sludge, said device comprising:
   a cylindrical container having an interior, a longitudinal axis, a sidewall having a height, a closed bottom, and a top having an opening, said sidewall being essentially transparent and being marked with an index of sludge volume;

a motor platform that rests on said opening, said motor platform supporting a housing that houses a motor which is attached to said platform, said housing having a motor off-on switch mounted thereon;

at least four vertically-oriented stator/legs, each stator/leg having a length, a top end and a bottom end and being connected at its top end to and extending below said motor platform into said container, said stator legs being connected together adjacent their bottom ends by means of an annular ring that fits inside said sidewall;

a vertically-oriented, rotatable shaft extending from said motor into said container along said longitudinal axis, said shaft having a length that is less than the length of said stator/legs and having a mixer blade attached thereto; and a sampling port affixed to and through said sidewall at approximately two-thirds of the sidewall height, said sampling port providing access to said interior.

2. The device of claim 1 further comprising:

means for quantifying the particulate content of a portion of said sample that has been removed from said container through said sampling port.

3. The device of claim 2 wherein:

said motor is an electric motor which is adapted to rotate said shaft at a substantially constant rotational speed to flocculate said sample for approximately a number of minutes after said sample is added to said container, said number of minutes being selected from the group consisting of
5 minutes,
10 minutes
20 minutes, and
30 minutes;

said index of sludge volume is adapted to provide a measurement of a volume of sludge solids in said container approximately 5 minutes after the rotation has ceased to produce a first measurement and again about 30 minutes after the rotation has ceased to produce a second measurement; and said means for quantifying is adapted to provide a measurement of the turbidity of said portion at about 30 minutes after the rotation has ceased to produce a third measurement.

4. The device of claim 3 further comprising:

means for collecting said sample and other sludge samples from the aeration tank of an activated sludge plant;

means for comparing said first measurement, said second measurement and said third measurement to measurements made on said other samples collected and characterized in the same way at different times in the past to determine whether the sludge quality characteristic quantified by each measurement has changed and, if so, the direction of change of each characteristic;

means for determining the presence or absence of change in any characteristic and the direction of change of any characteristic that has changed to produce a result; and means for processing said result by means of an algorithm to determine how to optimize the performance of said activated sludge plant.

5. The device of claim 4 further comprising:

means for determining averages that is adapted to determine a first average measurement, a second average measurement and a third average measurement by averaging a first plurality of first measurements, a second plurality of second measurements and a third plurality of third measurements, respectively, with each plurality of measurements characterizing a plurality of samples collected at essentially the same time.

6. The device of claim 5 further comprising:

means for determining variability that is adapted to determine a first standard deviation or range of measurements, a second standard deviation or range of measurements and a third standard deviation or range of measurements by calculating the standard deviation or range of a first plurality of first measurements, a second plurality of second measurements and a third plurality of third measurements, respectively, with each plurality of measurements characterizing a plurality of samples collected at essentially the same time.

7. The device of claim 5 or 6 further comprising:

means for controlling that is adapted to use said average measurements and said standard deviations or ranges of measurements to compare said average measurements to other average measurements of other pluralities of samples collected and characterized in the same way at different times in the past to determine whether any sludge quality characteristic quantified by each average measurement has changed and, if so, the direction of change of each characteristic to produce a signal; and means for processing said signal that is adapted to process the presence or absence of change in any characteristic and the direction of change of any characteristic that has changed by means of an algorithm to determine how to optimize the performance of said activated sludge plant by taking an action.

8. The device of claim 7 further comprising:

means for control charting that is adapted to determine the presence or absence of change and the direction of change by plotting said average measurements on control charts and by comparing said average measurements to control limits on said control charts.

9. The device of claim 8 further comprising:

knowledgebase processing means for determining flow rate changes; and means for taking said action;

wherein said action is selected from the group consisting of:
changing a return activated sludge rate,
changing a waste activated sludge rate, and
changing an aeration rate.

10. The device of claim 9 wherein:

said means for taking said action is adapted to change at least one of said rates by no more than ten percent.

11. A device for quantifying the quality of a sample of sludge in a container having an opening at its top, said device comprising:

a motor platform that rests on the opening in said container, said motor platform having a top side and a bottom side;

at least three vertically-oriented stator/legs connected to said bottom side and extending below said motor platform into said container, each of said stator/legs having a foot at its lower end;

a motor attached to said top side of said platform; and a vertically-oriented shaft extending from said motor into said container, said shaft having a length that is less than the length of said stator/legs and having a mixer blade attached thereto;

whereby said device may be removed from said container and rested in an upright position on the feet of said stator/legs.

12. The device of claim 11 further comprising:
means for measuring the height of the liquid/solids interface in said sample; and
means for quantifying the particulate content of a portion of said sample above said liquid/solids interface.

13. The device of claim 12 wherein:
said motor is an electric motor which is adapted to rotate said shaft at a substantially constant rotational speed to flocculate said sample for approximately 30 minutes after said sample is added to said container;
said means for measuring is adapted to measure said height approximately 5 minutes after the rotation has ceased to produce a first measurement and again about 30 minutes after the rotation has ceased to produce a second measurement; and
said means for quantifying is adapted to measure the particulate content of said portion at about 30 minutes after the rotation has ceased to produce a third measurement.

14. The device of claim 13 further comprising:
means for collecting said sample and other sludge samples from an activated sludge plant;
means for comparing said first measurement, said second measurement and said third measurement to measurements made on said other samples collected and characterized in the same way in the past to determine whether each measurement has changed and, if so, the direction of change of each measurement; and
means for determining the presence or absence of change in a measurement and the direction of change of any measurement that has changed to produce a result; and
means for processing said result by means of an algorithm to determine how to optimize the performance of said activated sludge plant by taking or not taking an action.

15. The device of claim 14 further comprising:
knowledgebase processing means for determining flow rate changes; and
means for taking said action;
wherein said action is selected from the group consisting of:
changing a return activated sludge rate,
changing a waste activated sludge rate, and
changing an aeration rate.

16. A device for measuring activated sludge quality and for controlling an activated sludge process comprising:
means for containing a plurality of samples of activated sludge obtained in a time sequence from said process, said means for containing having a top with an opening;
means for stirring said each sample;
means for measuring the height of a liquid/solids interface in each said sample;
means for measuring the particulate content of the portion of each said sample above said liquid/solids interface; and
means for controlling the activated sludge process;
wherein said means for stirring comprises:
a motor platform that rests on the opening in the top of said means for containing, said motor platform having a top side;
at least three vertically-oriented stator/legs connected to and extending below said motor platform into said means for containing;
a motor attached to the top side of said platform; and
a vertically-oriented shaft extending below said motor into said means for containing, said shaft having a length that is less than the length of said stator/legs and having a mixer blade attached thereto.

17. The device of claim 16 wherein said means for controlling comprises:
means for changing a return activated sludge rate;
means for changing a waste activated sludge rate;
means for changing an aeration rate; and
means for determining whether one or more of the means for changing should be used, and, if so, how.

18. The device of claim 17 wherein the means for determining comprises:
means for accessing a knowledgebase of rules concerning how to modify the operation of said process.

19. The device of claim 18 further comprising:
primary rule-processing means wherein said means for accessing a knowledgebase is adapted to access one or more rules selected from the following group:
if the sludge settling characteristic, the sludge compaction characteristic and the sludge flocculation characteristic are unchanged, do not make a process control change;
if the sludge flocculation characteristic has decreased and the other characteristics have not changed, do not make a process control change and adjust said control limits if long lived;
if the sludge flocculation characteristic has increased and the other characteristics have not changed, increase the aeration rate;
if the sludge compaction characteristic has decreased and the other characteristics have not changed, check the return activated sludge rate and increase it if necessary;
if the sludge settling characteristic has not changed, the sludge compaction characteristic has decreased and the sludge flocculation characteristic has decreased, confirm that the return activated sludge rate has not changed, make no other process control changes and adjust said control limits if long lived;
if the sludge settling characteristic has not changed, the sludge compaction characteristic has decreased and the sludge flocculation characteristic has increased, confirm that the aeration rate has not changed and either decrease it or increase it, as appropriate;
if the sludge settling characteristic has not changed, the sludge compaction characteristic has increased and the sludge flocculation characteristic has not changed, confirm that early filamentous organism growth is occurring and, depending on filament, make appropriate process control changes;
if the sludge settling characteristic has decreased, the sludge compaction characteristic has not changed and the sludge flocculation characteristic has not changed, make no process control changes and adjust said control limits accordingly, if long lived;
if the sludge settling characteristic has decreased, the sludge compaction characteristic has increased and the sludge flocculation characteristic has not changed, increase the waste activated sludge rate;
if the sludge settling characteristic has decreased, the sludge compaction characteristic has increased and the sludge flocculation characteristic has decreased, increase the return activated sludge rate, increase the waste activated sludge rate and increase the aeration rate;

if the sludge settling characteristic has increased, the sludge compaction characteristic has not changed and the sludge flocculation characteristic has not changed, make no process control changes;

if the sludge settling characteristic has increased, the sludge compaction characteristic has not changed and the sludge flocculation characteristic has increased, make no process control changes; and if the sludge settling characteristic has increased, the sludge compaction characteristic has decreased and the sludge flocculation characteristic has decreased, increase the return activated sludge rate and increase the waste activated sludge rate.

20. The device of claim 19 further comprising:

secondary rule-processing means wherein said means for accessing a knowledgebase is adapted to access the rule that if sludge quality characteristics change in a way that is not listed in claim 19, make no process control changes.

21. A method for optimizing the operation of an activated sludge process, said method comprising the steps of:

collecting a first group of data on the settling, compacting and flocculating characteristics of an activated sludge at a first point in time;

collecting a second group of data on the settling, compacting and flocculating characteristics at a second point in time;

comparing said first group of data to said second group of data to determine whether one or more of said characteristics has changed significantly, and, if so, in which direction;

accessing a knowledgebase of rules concerning how to modify the operation of said activated sludge process depending on whether one or more of said characteristics has changed, and, if so, in which direction;

determining an activated sludge process operating strategy; and implementing said strategy to control said activated sludge process.

22. The method of claim 21 wherein both of said collecting steps include:

obtaining a sample of activated sludge at a plurality of times during a day;

placing each sample into a container;

stirring each sample for approximately 5 to 30 minutes after each sample is added to said container;

measuring the height of the interface of the liquids and solids in each sample approximately 5 minutes after said stirring has ceased to produce a first plurality of measurements and again about 30 minutes after said stirring has ceased to produce a second plurality of measurements; and measuring the particulate content of the portion of each sample above said interface at about 30 minutes after stirring has stopped to produce a third plurality of measurements.

23. The method of claim 22 wherein said comparing step includes:

calculating the average and range of each plurality of measurements;

plotting the average of each plurality of measurements on a control chart;

plotting the range of each plurality of measurements on the control chart;

after a plurality of days, estimating the population mean and standard deviation of each measurement;

plotting a central control line, an upper control limit and a lower control limit on the control chart;

assessing whether the activated sludge process is in a state of statistical control;

reevaluating, refining and replotting said central control line, said upper control limit and said lower control limit; and as each average and range is plotted, determining whether one or more of said characteristics has changed significantly, and, if so, in which direction.

24. The method of claim 21, 22 or 23 in which said knowledgebase contains one or more rules selected from the following group:

if the sludge settling characteristic, the sludge compaction characteristic and the sludge flocculation characteristic are unchanged, do not make a process control change;

if the sludge flocculation characteristic has decreased and the other characteristics have not changed, do not make a process control change and adjust said control limits if long lived; and if the sludge flocculation characteristic has increased and the other characteristics have not changed, increase the aeration rate.

25. The method of claim 21, 22 or 23 in which said knowledgebase contains one or more rules selected from the following group:

if the sludge compaction characteristic has decreased and the other characteristics have not changed, increase the return activated sludge rate;

if the sludge settling characteristic has not changed, the sludge compaction characteristic has decreased and the sludge flocculation characteristic has decreased, confirm that the return activated sludge rate has not changed, make no other process control changes and adjust said control limits if long lived; and if the sludge settling characteristic has not changed, the sludge compaction characteristic has decreased and the sludge flocculation characteristic has increased, confirm that the aeration rate has not changed and either decrease it or increase it, as appropriate.

26. The method of claim 21, 22 or 23 in which said knowledgebase contains one or more rules selected from the following group:

if the sludge settling characteristic has not changed, the sludge compaction characteristic has increased and the sludge flocculation characteristic has not changed, confirm that early filamentous organism growth is occurring and, depending on filament, make appropriate process control changes;

if the sludge settling characteristic has not changed, the sludge compaction characteristic has increased and the sludge flocculation characteristic has decreased, do not make a process control change; and if the sludge settling characteristic has not changed, the sludge compaction characteristic has increased and the sludge flocculation characteristic has increased, do not make a process control change.

27. The method of claim 21, 22 or 23 in which said knowledgebase contains one or more rules selected from the following group:

if the sludge settling characteristic has decreased, the sludge compaction characteristic has not changed and the sludge flocculation characteristic has not changed, make no process control changes and adjust said control limits accordingly, if long lived;

if the sludge settling characteristic has decreased, the sludge compaction characteristic has not changed and the sludge flocculation characteristic has decreased, do not make a process control change; and if the sludge settling characteristic has decreased, the sludge compaction characteristic has not changed and the sludge flocculation characteristic has decreased, do not make a process control change.

28. The method of claim 21, 22 or 23 in which said knowledgebase contains one or more rules selected from the following group:

if the sludge settling characteristic has decreased, the sludge compaction characteristic has decreased and the sludge flocculation characteristic has not changed, do not make a process control change;

if the sludge settling characteristic has decreased, the sludge compaction characteristic has decreased and the sludge flocculation characteristic has decreased, do not make a process control change; and if the sludge settling characteristic has decreased, the sludge compaction characteristic has decreased and the sludge flocculation characteristic has increased, do not make a process control change.

29. The method of claim 21, 22 or 23 in which said knowledgebase contains one or more rules selected from the following group:

if the sludge settling characteristic has decreased, the sludge compaction characteristic has increased and the sludge flocculation characteristic has not changed, increase the waste activated sludge rate; and if the sludge settling characteristic has decreased, the sludge compaction characteristic has increased and the sludge flocculation characteristic has decreased, increase the return activated sludge rate, increase the waste activated sludge rate and increase the aeration rate.

30. The method of claim 21, 22 or 23 in which said knowledgebase contains one or more rules selected from the following group:

if the sludge settling characteristic has increased, the sludge compaction characteristic has not changed and the sludge flocculation characteristic has not changed, do not make a process control change;

if the sludge settling characteristic has increased, the sludge compaction characteristic has not changed and the sludge flocculation characteristic has decreased, do not make a process control change; and if the sludge settling characteristic has increased, the sludge compaction characteristic has not changed and the sludge flocculation characteristic has increased, do not make a process control change.

31. The method of claim 21, 22 or 23 in which said knowledgebase contains one or more rules selected from the following group:

if the sludge settling characteristic has increased, the sludge compaction characteristic has decreased and the sludge flocculation characteristic has not changed, do not make a process control change;

if the sludge settling characteristic has increased, the sludge compaction characteristic has decreased and the sludge flocculation characteristic has decreased, increase the return activated sludge rate and increase the waste activated sludge rate; and if the sludge settling characteristic has increased, the sludge compaction characteristic has decreased and the sludge flocculation characteristic has increased, do not make a process control change.

32. The method of claim 21, 22 or 23 in which said knowledgebase contains one or more rules selected from the following group:

if the sludge settling characteristic has increased, the sludge compaction characteristic has increased and the sludge flocculation characteristic has not changed, do not make a process control change;

if the sludge settling characteristic has increased, the sludge compaction characteristic has increased and the sludge flocculation characteristic has decreased, do not make a process control change; and if the sludge settling characteristic has increased, the sludge compaction characteristic has increased and the sludge flocculation characteristic has increased, do not make a process control change.

33. An activated sludge plant comprising:

an activated sludge process unit controlled using the method of claim 21, 22 or 23.

34. A system for optimizing the operation of an activated sludge process, said system comprising:

means for collecting a first group of data on the settling, compacting and flocculating characteristics of an activated sludge at a first point in time;

means for collecting a second group of data on the settling, compacting and flocculating characteristics of the activated sludge at a second point in time;

means for comparing said first group of data to said second group of data to determine whether one or more of said characteristics has changed significantly, and, if so, in which direction;

means for accessing a knowledgebase of rules concerning how to modify the operation of said activated sludge process depending on whether one or more of said characteristics has changed, and, if so, in which direction;

means for determining an activated sludge process operating strategy; and means for implementing said strategy to control said activated sludge process.

35. A system for controlling the operation of an activated sludge plant comprising an aeration basin, a clarifier, a return activated sludge pump, a waste activated sludge pump and a blower, said system comprising:

a computer having a processor, a memory and a monitor;

a sensing and control circuit connected to said computer;

a sludge quality sensor for sensing the settling characteristics, the compacting characteristics and the flocculating characteristics of sludge withdrawn from said aeration basin, said sensor being connected to said circuit;

a plurality of instructions stored in said memory causing the computer implement a sequence of steps including:

at regular intervals, activating a pump for collecting of a sample of activated sludge from said aeration basin and depositing it in said sludge quality sensor;

activating a mixer to stir each sample for a first set number of minutes;

a second set number of minutes after stirring ceases, activating a sludge blanket depth senor to measure the distance the interface between the solids and liquids in each sample drops and to produce a first output signal;

a third set number of minutes after stirring ceases, activating said sludge blanket depth senor to measure the distance the interface between the solids and liquids in each sample drops and to produce a second output signal;

activating a turbidimeter to measure the turbidity of the supernatant in said sludge quality sensor and to produce a third output signal;

draining said sludge quality sensor;

transmitting each of said signals to said processor via said sensing and control circuit to produce a current group of data;

comparing a plurality of groups of data collected in the same way to said current group of data;

determining whether the settling, compacting and/or flocculating characteristic(s) of said sludge have changed, and, if so, in which direction;

accessing a knowledgebase of rules concerning how to modify the operation of said plant depending on whether one or more of said characteristics has changed, and, if so, in which direction;

determining an activated sludge process operating strategy; and implementing said strategy to control said activated sludge plant.

36. An activated sludge plant comprising the system of claim 34 or 35.

37. A method for optimizing the operation of an activated sludge process, said method comprising:

introducing a first sample of activated sludge from said process into the device of claim 1;

collecting a first group of data on the settling, compacting and flocculating characteristics of the first sample of activated sludge at a first point in time;

introducing a second sample of activated sludge from said process into the device of claim 1;

collecting a second group of data on the settling, compacting and flocculating characteristics of the second sample of activated sludge at a second point in time;

comparing said first group of data to said second group of data to determine whether one or more of said characteristics has changed significantly, and, if so, in which direction;

accessing a knowledgebase of rules concerning how to modify the operation of said activated sludge process depending on whether one or more of said characteristics has changed, and, if so, in which direction;

determining an activated sludge process operating strategy; and implementing said strategy to control said activated sludge process.

38. A method for optimizing the operation of an activated sludge process, said method comprising the steps of:

collecting a first group of data on the settling, compacting and flocculating characteristics of an activated sludge at a first point in time;

collecting a second group of data on the settling, compacting and flocculating characteristics of the activated sludge at a second point in time;

comparing said first group of data to said second group of data to determine whether one or more of said characteristics has changed significantly, and, if so, in which direction;

accessing a knowledgebase of rules concerning how to modify the operation of said activated sludge process depending on whether one or more of said characteristics has changed, and, if so, in which direction;

determining an activated sludge process operating strategy; and implementing said strategy to control said activated sludge process;

wherein both of said collecting steps include:

obtaining a sample of activated sludge at a plurality of times during a day;

placing each sample into the device of claim 10;

stirring each sample for approximately 5 to 30 minutes after each sample is added to said device;

measuring the height of the interface of the liquids and solids in each sample approximately 5 minutes after said stirring has ceased to produce a first plurality of measurements and again about 30 minutes after said stirring has ceased to produce a second plurality of measurements; and measuring the particulate content of the portion of each sample above said interface at about 30 minutes after stirring has stopped to produce a third plurality of measurements; and wherein said comparing step includes:

calculating the average and range of each plurality of measurements;

plotting the average of each plurality of measurements on a control chart;

plotting the range of each plurality of measurements on the control chart;

after a plurality of days, estimating the population mean and standard deviation of each measurement;

plotting a central control line, an upper control limit and a lower control limit on the control chart;

assessing whether the activated sludge process is in a state of statistical control;

reevaluating, refining and replotting said central control line, said upper control limit and said lower control limit; and as each average and range is plotted, determining whether one or more of said characteristics has changed significantly, and, if so, in which direction.

39. A method for optimizing the operation of an activated sludge process, said method comprising the steps of:

collecting a first group of data on the settling, compacting and flocculating characteristics of an activated sludge at a first point in time;

collecting a second group of data on the settling, compacting and flocculating characteristics of the activated sludge at a second point in time;

comparing said first group of data to said second group of data to determine whether one or more of said characteristics has changed significantly, and, if so, in which direction;

accessing a knowledgebase of rules concerning how to modify the operation of said activated sludge process depending on whether one or more of said characteristics has changed, and, if so, in which direction;

determining an activated sludge process operating strategy; and implementing said strategy to control said activated sludge process;

wherein both of said collecting steps include:

obtaining a sample of activated sludge at a plurality of times during a day;

placing each sample into the device of claim 15;

stirring each sample for approximately 5 to 30 minutes after each sample is added to said device;

measuring the height of the interface of the liquids and solids in each sample approximately 5 minutes after said stirring has ceased to produce a first plurality of measurements and again about 30 minutes after said stirring has ceased to produce a second plurality of measurements; and measuring the particulate content of the portion of each sample above said interface at about 30 minutes after stirring has stopped to produce a third plurality of measurements; and wherein said comparing step includes:

calculating the average and range of each plurality of measurements;

plotting the average of each plurality of measurements on a control chart;

plotting the ranges of each plurality of measurements on the control chart;

after a plurality of days, estimating the population mean and standard deviation of each measurement;

plotting a central control line, an upper control limit and a lower control limit on the control chart;

assessing whether the activated sludge process is in a state of statistical control;

reevaluating, refining and replotting said central control line, said upper control limit and said lower control limit; and as each average and range is plotted, determining whether one or more of said characteristics has changed significantly, and, if so, in which direction.

40. A method for operating an activated sludge process, said method comprising:

introducing wastewater into the activated sludge plant of claim 33, said activated sludge plant being used to grow an activated sludge;

collecting a first group of data on the settling, compacting and flocculating characteristics of the activated sludge at a first point in time;

collecting a second group of data on the settling, compacting and flocculating characteristics of the activated sludge at a second point in time;

comparing said first group of data to said second group of data to determine whether one or more of said characteristics has changed significantly, and, if so, in which direction;

accessing a knowledgebase of rules concerning how to modify the operation of said plant depending on whether one or more of said characteristics has changed, and, if so, in which direction;

determining an activated sludge process operating strategy; and implementing said strategy to control said activated sludge process;

wherein both of said collecting steps include:

obtaining a sample of activated sludge at a plurality of times during a day;

placing each sample into a device;

stirring each sample for approximately 5 to 30 minutes after said sample is added to said device;

measuring the height of the interface of the liquids and solids in each sample approximately 5 minutes after said stirring has ceased to produce a first plurality of measurements and again about 30 minutes after said stirring has ceased to produce a second plurality of measurements; and measuring the particulate content of the portion of each sample above said interface at about 30 minutes after stirring has stopped to produce a third plurality of measurements.

41. A method for optimizing the operation of an activated sludge process, said method comprising:

introducing wastewater into the activated sludge plant of claim 36;

collecting a first group of data on the settling, compacting and flocculating characteristics of the activated sludge at a first point in time;

collecting a second group of data on the settling, compacting and flocculating characteristics of the activated sludge at a second point in time;

comparing said first group of data to said second group of data to determine whether one or more of said characteristics has changed significantly, and, if so, in which direction;

accessing a knowledgebase of rules concerning how to modify the operation of said plant depending on whether one or more of said characteristics has changed, and, if so , in which direction;

determining an activated sludge process operating strategy; and implementing said strategy to control said activated sludge process.

42. A method for optimizing the operation of an activated sludge process, said method comprising:

operating the system of claim 35;

collecting a first group of data on the settling, compacting and flocculating characteristics of the activated sludge at a first point in time;

collecting a second group of data on the settling, compacting and flocculating characteristics of the activated sludge at a second point in time;

comparing said first group of data to said second group of data to determine whether one or more of said characteristics has changed significantly, and, if so, in which direction;

accessing a knowledgebase of rules concerning how to modify the operation of said plant depending in whether one or more of said characteristics has changed, and, if so, in which direction;

determining an activated sludge process operating strategy; and implementing said strategy to control said activated sludge process.

* * * * *